US 6,558,357 B1

(12) United States Patent
Hoeck

(10) Patent No.: US 6,558,357 B1
(45) Date of Patent: May 6, 2003

(54) HYPODERMIC SYRINGE WITH SELECTIVELY RETRACTABLE NEEDLE

(75) Inventor: Roger W. Hoeck, Holdrege, NE (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 88 days.

(21) Appl. No.: 09/651,520

(22) Filed: Aug. 30, 2000

(51) Int. Cl.$^7$ .................................. A61M 5/32
(52) U.S. Cl. ................ 604/195; 604/110; 604/242; 128/919
(58) Field of Search ................ 604/111, 110, 604/187, 192, 194, 195–198, 207–211, 218, 220, 227, 234, 236, 240–243; 128/919

(56) References Cited

U.S. PATENT DOCUMENTS

| | | |
|---|---|---|
| 4,233,975 A | 11/1980 | Yerman |
| 4,838,863 A | 6/1989 | Allard et al. |
| 4,838,869 A | 6/1989 | Allard |
| 4,900,307 A | 2/1990 | Kulli |
| 4,927,414 A | 5/1990 | Kulli |
| 4,929,232 A * | 5/1990 | Sweeney et al. ............ 604/111 |
| 4,929,237 A | 5/1990 | Medway |
| 4,946,446 A | 8/1990 | Vadher |
| 4,955,870 A | 9/1990 | Ridderheim et al. |
| 4,966,593 A | 10/1990 | Lennox |
| 4,973,316 A | 11/1990 | Dysarz |
| 4,994,034 A | 2/1991 | Botich et al. |
| 5,011,476 A | 4/1991 | Foster |
| 5,013,301 A | 5/1991 | Marotta, Jr. et al. |
| 5,019,044 A | 5/1991 | Tsao |
| 5,045,063 A | 9/1991 | Spielberg |
| 5,046,508 A | 9/1991 | Weissler |
| 5,047,017 A | 9/1991 | Koska |
| 5,049,133 A | 9/1991 | Villen Pascual |
| 5,053,010 A | 10/1991 | McGary et al. |
| 5,064,419 A | 11/1991 | Gaarde |

(List continued on next page.)

FOREIGN PATENT DOCUMENTS

| | | |
|---|---|---|
| EP | 0 596 211 A1 | 5/1994 |
| EP | 0 704 225 A2 | 4/1996 |

Primary Examiner—Manuel Mendez
Assistant Examiner—Michael M. Thompson
(74) Attorney, Agent, or Firm—Jeanne P. Lukasavage; John L. Voellmicke

(57) ABSTRACT

A hypodermic syringe with a selectively retractable includes an barrel having an proximal end and a distal end that defines a receiver with a shoulder. The barrel has a hollow bore therethrough and the receiver includes a plurality of inwardly projecting cams distal to the shoulder. There is an elongate plunger with a proximal end and a distal end sized to fit slidably within the bore of the barrel to define a chamber. There is a hub with a flange and a stem that has a passageway therethrough extending distally into the receiver. The stem has distal recesses disposed to engage the projecting cams so that the hub is retained with the distal end of the stem in the receiver. The syringe includes a needle mounted in the passageway in the hub with the distal point projecting distally and the fluid path communicates with the chamber. There is a clip about the elongate plunger initially allowing movement of the plunger for drawing and expelling fluid. When sufficient distal force is applied to the plunger moving and rotates the hub, the clip engages the barrel permitting only proximal movement of the plunger. The syringe includes a spring disposed about the stem compressed between the flange and the inward shoulder. When sufficient distal force is applied to the flange the hub is no longer retained. The spring urges a proximal movement into the barrel as the plunger is moved proximally.

13 Claims, 12 Drawing Sheets

U.S. PATENT DOCUMENTS

| | | | |
|---|---|---|---|
| 5,078,698 A | * | 1/1992 | Stiehl et al. .................. 604/235 |
| 5,084,018 A | | 1/1992 | Tsao |
| 5,084,029 A | | 1/1992 | Nacci nee Tagliaferri et al. |
| 5,085,640 A | | 2/1992 | Gibbs |
| 5,092,853 A | | 3/1992 | Couvertier, II |
| 5,114,410 A | | 5/1992 | Caralt Batlle |
| 5,180,369 A | | 1/1993 | Dysarz |
| 5,180,370 A | | 1/1993 | Gillespie |
| 5,188,599 A | | 2/1993 | Botich et al. |
| 5,201,710 A | | 4/1993 | Caselli |
| 5,211,629 A | | 5/1993 | Pressly et al. |
| 5,232,447 A | | 8/1993 | Schwarz et al. |
| 5,232,456 A | | 8/1993 | Gonzalez |
| 5,267,961 A | | 12/1993 | Shaw |
| 5,267,976 A | | 12/1993 | Guerineau et al. |
| 5,342,308 A | | 8/1994 | Boschetti |
| 5,376,080 A | | 12/1994 | Petrussa |
| 5,385,551 A | | 1/1995 | Shaw |
| 5,389,076 A | | 2/1995 | Shaw |
| 5,395,337 A | | 3/1995 | Clemens et al. |
| 5,407,431 A | | 4/1995 | Botich et al. |
| 5,407,436 A | | 4/1995 | Toft et al. |
| 5,423,758 A | | 6/1995 | Shaw |
| 5,433,712 A | * | 7/1995 | Stiles et al. .................. 604/110 |
| 5,487,732 A | | 1/1996 | Jeffrey |
| 5,531,694 A | | 7/1996 | Clemens et al. |
| 5,542,927 A | | 8/1996 | Thorne et al. |
| 5,562,629 A | | 10/1996 | Haughton et al. |
| 5,573,510 A | | 11/1996 | Isaacson |
| 5,575,777 A | | 11/1996 | Cover et al. |
| 5,578,011 A | | 11/1996 | Shaw |
| 5,605,544 A | | 2/1997 | Tsao |
| 5,613,952 A | | 3/1997 | Pressly, Sr. et al. |
| 5,632,733 A | | 5/1997 | Shaw |
| 5,634,909 A | | 6/1997 | Schmitz |
| 5,637,092 A | | 6/1997 | Shaw |
| 5,643,211 A | | 7/1997 | Sadowski et al. |
| 5,681,292 A | | 10/1997 | Tober et al. |
| 5,685,863 A | | 11/1997 | Botich et al. |
| 5,762,634 A | * | 6/1998 | Davis .......................... 604/195 |
| 5,769,822 A | | 6/1998 | McGary et al. |
| 5,782,804 A | | 7/1998 | McMahon |
| 5,788,677 A | | 8/1998 | Botich et al. |
| 5,792,107 A | | 8/1998 | Petrocelli |
| 5,800,395 A | | 9/1998 | Botich et al. |
| 5,800,403 A | | 9/1998 | Pressly, Sr et al. |
| 5,853,390 A | | 12/1998 | Freschi |
| 5,882,342 A | | 3/1999 | Cooper et al. |
| 5,885,257 A | | 3/1999 | Badger |
| 5,935,104 A | | 8/1999 | Janek et al. |
| 5,984,898 A | | 11/1999 | Garvin |
| 6,004,278 A | | 12/1999 | Botich et al. |
| 6,010,486 A | | 1/2000 | Carter et al. |

* cited by examiner

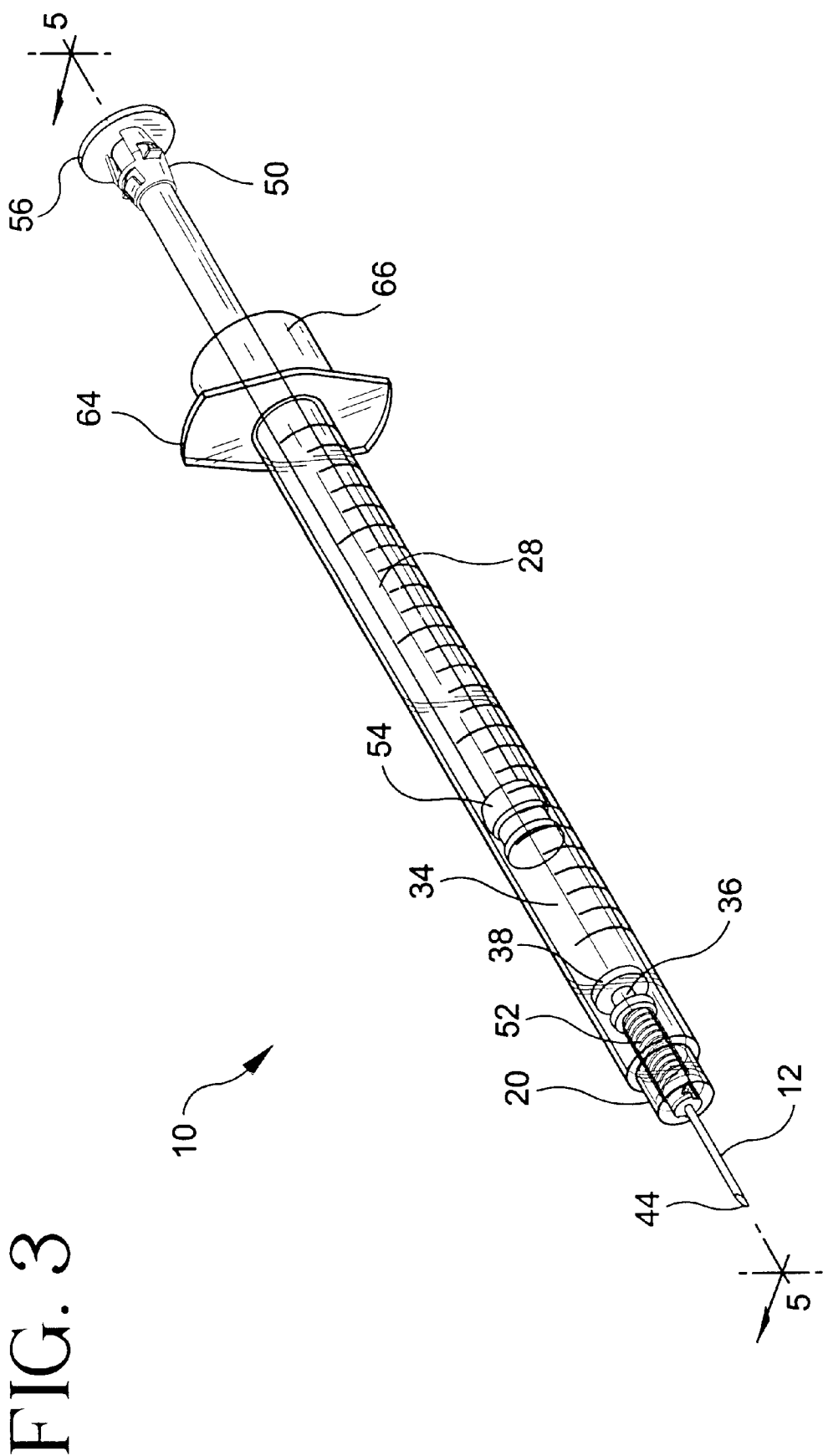

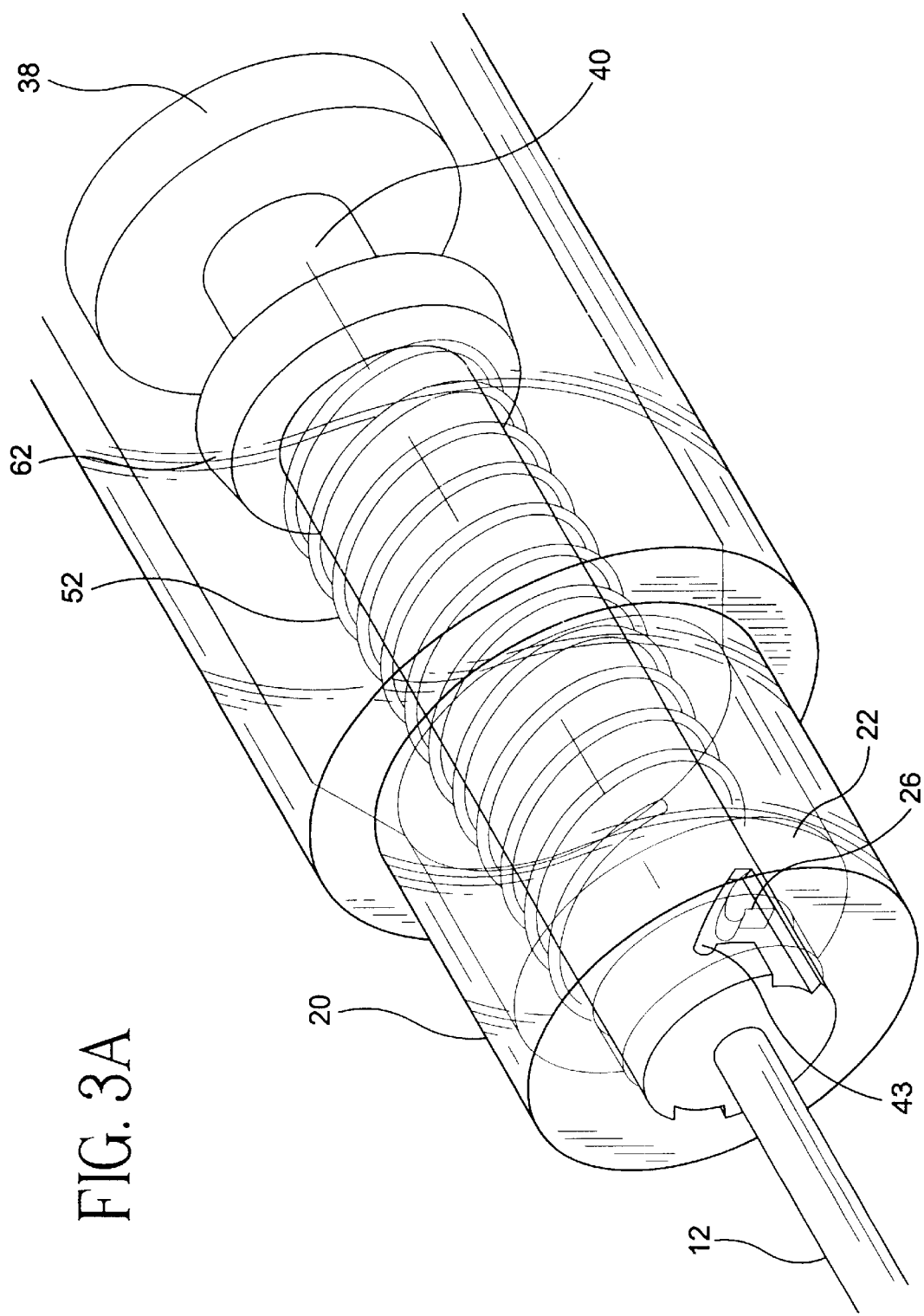

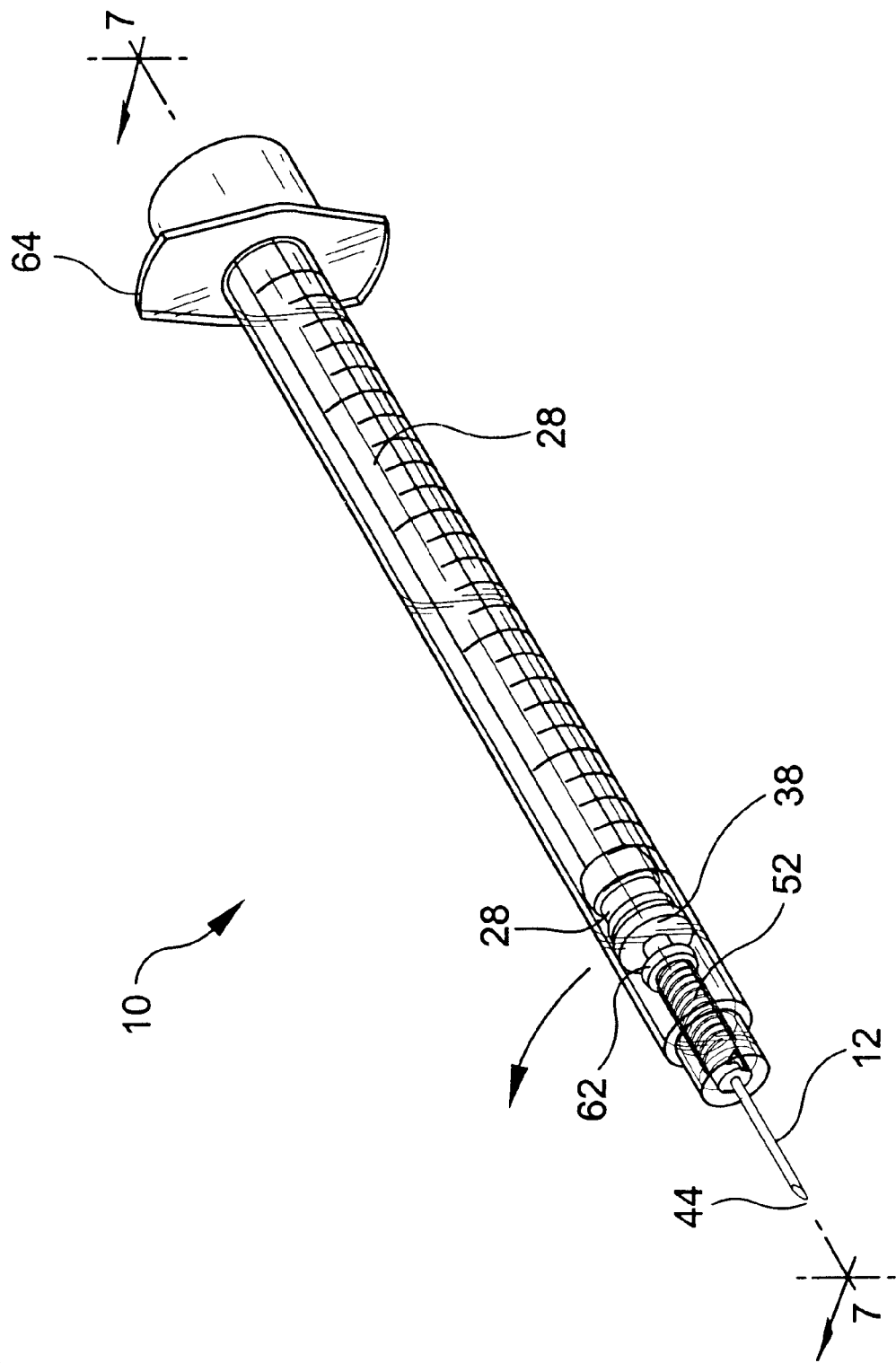

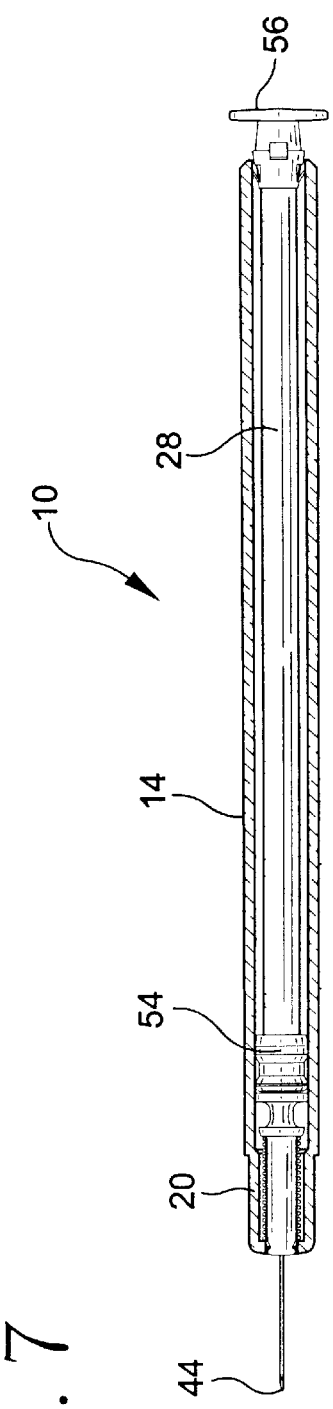
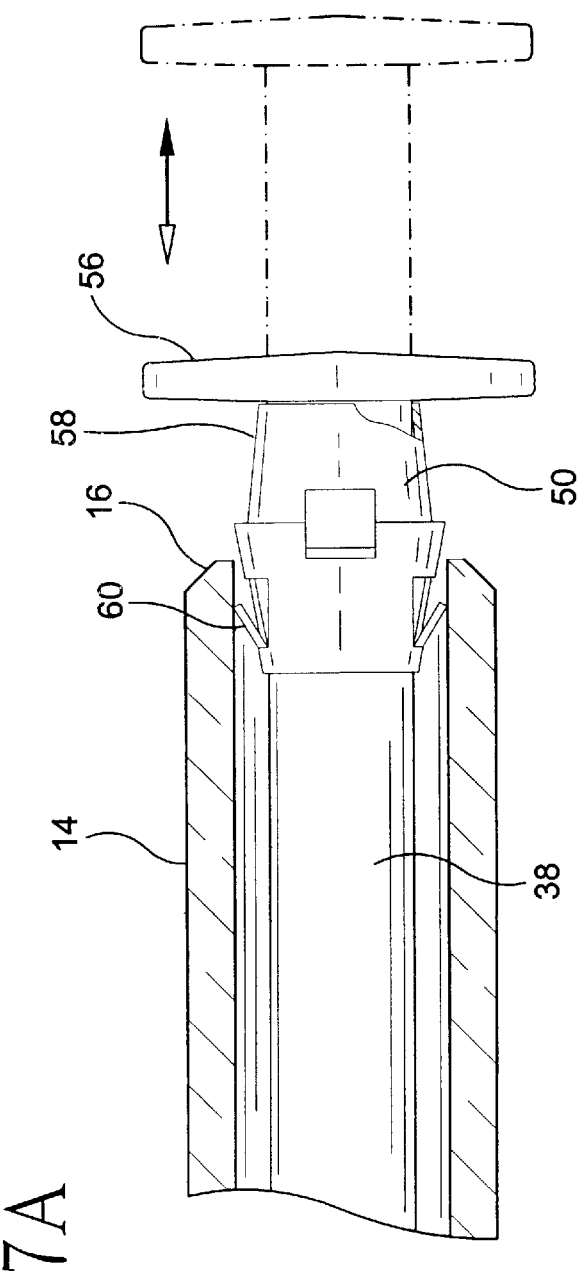
FIG. 7
FIG. 7A

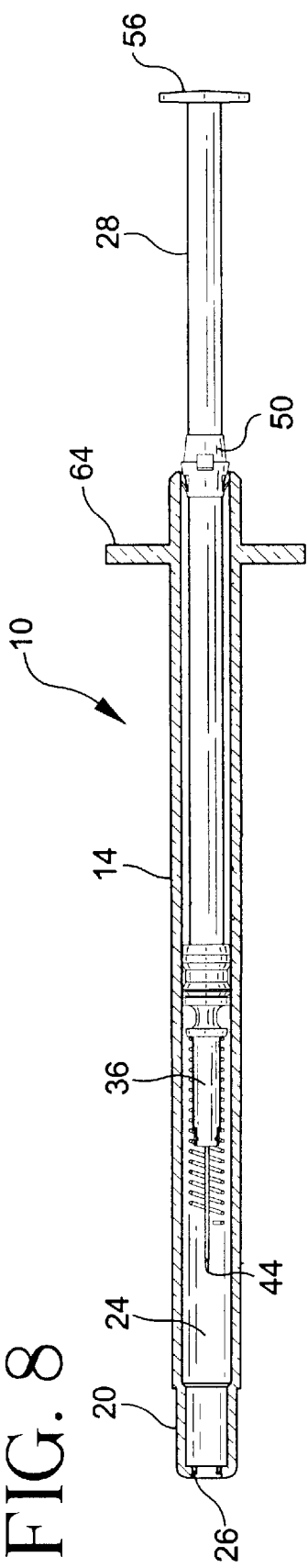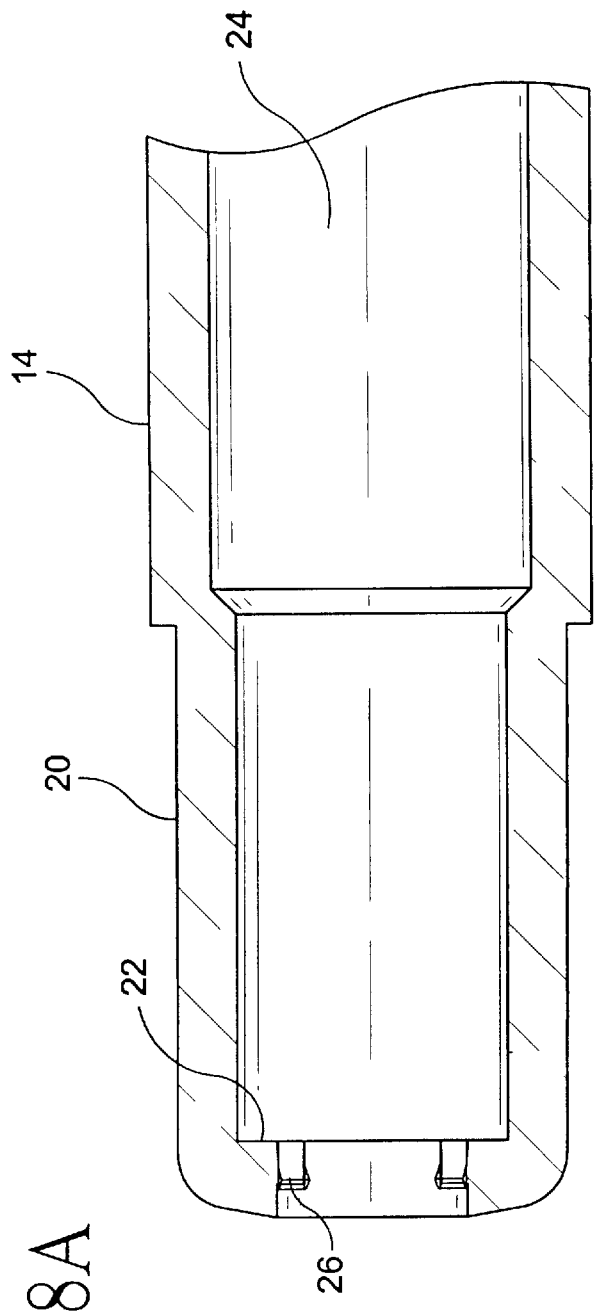
FIG. 8
FIG. 8A

HYPODERMIC SYRINGE WITH SELECTIVELY RETRACTABLE NEEDLE

FIELD OF INVENTION

The present invention is generally related to hypodermic syringes and more particularly to syringes that include a needle that is retractable after the intended use to substantially prevent inadvertent exposure to the needle and reuse of the syringe.

BACKGROUND

Hypodermic syringes are widely used in the medical arts for administering medicaments and for drawing body fluid samples. Generally, hypodermic syringes have a metal needle attached either fixedly or removably that has a sharpened distal point for penetrating vial stoppers or patient's skin. The hypodermic syringes and needles have been used for many years with few problems reported when the vast numbers and needles being used are considered. More recently, with the recognition of viral diseases that are transmitted by body fluids and greater sensitivity of the need to protect health care workers from inadvertent contact with previously used needles (commonly referred to as "sharps") as well as the need to reduce criminal misuse of improperly disposed of needles and syringes, syringes and needles that include provisions to prevent reuse have been developed.

Provisions intended to prevent reuse of needles and syringes include a variety of sharps collector systems that are widely used in health care facilities. Other developments include needle attachments that may be readily broken off by practitioners once the syringe has completed its intended use. A variety of shielding mechanisms has been developed; some of which are currently commercially available. While many of these developments have reduced the incidence of inadvertent exposure of healthcare workers to sharps, most of these devices can readily be overcome by an individual determined to obtain and misuse a hypodermic syringe and needle. As a result of this problem, further developments in the art of hypodermic syringes have resulted in syringes with needles that withdraw into the body of the syringe once their intended use is completed.

U.S. Pat. No. 4,838,869 discloses a retractable hypodermic needle configured for one time use wherein the needle is spring loaded and automatically irretrievably retracted into the hypodermic syringe when the syringe plunger is fully depressed, whereby protrusions on the end of the plunger engage tabs holding the spring loaded needle to release the needle for retraction. A potential problem with the design disclosed in this patent is that many times a practitioner may draw and expel a fluid several times during preparation for administration of a medicament and, with this design, the practitioner could inadvertently discharge the retraction mechanism. Further, the design would be very difficult to manufacture in large volumes.

U.S. Pat. No. 4,900,307 discloses a hypodermic needle with an enlarged hub that provides provisions for selectively withdrawing the needle into the hub once the syringe and needle have completed their intended usage. While this disclosed design does substantially eliminate the problem of premature discharge of the retraction mechanism, the enlarged hub has a considerable "dead volume" that would result in a significant undeliverable retention of the medicament. Additionally, although the needle is secured in the hub after discharge, the syringe itself is still fully functional after the hub with the needle inside is removed.

U.S. Pat. No. 4,994,034 discloses a hypodermic injection system with a retractable needle wherein the needle retracts within the interior cavity of a syringe plunger. The disclosed invention includes a cylindrical spring housing with resilient fingers which capture a coiled spring that biasly holds a needle holder against the retaining force of the resilient fingers. The plunger in this disclosure has a frangible end, which when engaging the resilient fingers under a predetermined amount of force, dissociate which remaining inwardly-tapered shoulders spread the resilient fingers, allowing the coiled spring to eject the needle and its holder into the interior cavity of the syringe plunger. A syringe manufactured using this disclosure would be complex and difficult to assemble. It is believed that no successful commercial product has been produced using this disclosure.

U.S. Pat. No. 5,019,044 discloses a safety hypodermic syringe with a hypodermic needle fixed connected to a holder plate and constantly supported by a spring for making axial movement. The holder plate is normally retained by a clamp at a ready position for injection. When the plunger of the syringe is pushed to the bottom of the barrel, the needle is released from the clamp and is pushed by the spring to drop and further follow a rubber plug to be squeezed into a chamber in the plunger. Again, no successful commercial product has resulted from this disclosure, which would be complex to manufacture and appears to have a considerable undeliverable dead volume.

Another example of a syringe with a retractable needle is disclosed in U.S. Pat. No. 5,053,010. The disclosed syringe retracts the needle into a hollow plunger with additional pressure on the plunger after the contents of the syringe are expelled. The disclosed design incorporates a sliding elastomeric seal which displaces from its forward position to a retracted position, thereby allowing additional forward travel of the plunger to actuate the retraction mechanism. A problem reported with this design is that, because of the soft nature of the seal, the seal may be prematurely displaced during its use in an injection. Attempts to overcome this difficulty by increasing the stiffness of the sealing member could impair the seal integrity.

U.S. Pat. No. 5,180,369 discloses a self destructive syringe assembly having a needle cannula fixed to a slidable piston. The slidable piston and slidable piston flange are held within the barrel of the syringe assembly by a compressed spring, a guide tube and a shatter ring. The plunger of the syringe assembly is a hollow elongated tube with a thumb flat at one end, a sliding gasket, a plunger shatter plate and a hook rim at the other end. The patent reports that when medicament is injected, the elongated hollow plunger is further thrust into the shatter ring, the shatter ring shatters, further allowing the slidable piston and slidable piston flange to thrust into the plunger shatter plate to shatter. The shattering of the plunger shatter plate causes the slidable piston and needle cannula to be thrust into the hollow plunger by the spring and is thus prevented from re-entering the guide tube. Again, no successful commercial product has resulted from this disclosure.

U.S. Pat. No. 5,180,370 discloses a syringe that has an internal mechanism for retracting the needle into the syringe after the injection has been given. In one disclosed embodiment, the needle is manually retracted by pulling back on the plunger, and in another, the needle is propelled by a compressed spring into a hollow chamber within the plunger. A syringe produced with this disclosure would be complex to manufacture, and no successful commercial product has resulted from this disclosure.

U.S. Pat. No. 5,188,599 discloses a hypodermic injection system with a needle that retracts within an interior cavity of the syringe plunger. The needle when retracted is held within the plunger. The disclosed device includes a cylindrical spring housing that has resilient fingers which capture a spring under bias holding a needle holder against the retaining force of resilient fingers. The plunger has a frangible end which dissociates when the outwardly tapered shoulders spread the resilient fingers, allowing the coiled spring to eject the needle and its holder into the interior cavity of the syringe plunger. The patent also discloses a body fluid sampling device that includes a double-ended needle for communication with an evacuated blood collection tube. This patent also includes a review of several earlier disclosures related to retractable needles. Attempts have been made to produce commercial products based on the disclosures of this patent, but as yet there is no successful commercial product.

U.S. Pat. No. 5,201,710 discloses a syringe fitted with a clamping device for the needle and with a mechanism to enable the needle to be automatically retractable into the syringe body at the end of an injection. The disclosed device includes inner and outer cylinders, openings at the ends of the outer cylinder, a third opening at an end of the inner cylinder and a closure for the third opening. The disclosed device further includes a needle with a head, a seal, a first spring to push the needle against the closure and a clamping device loaded by a second spring to maintain outward to the syringe and to release the needle. There is a diaphragm in the closure that bends before breaking and a sharp element to break the diaphragm. There also is a closure to prevent the needle from being accessible and a stop to prevent the second cylinder from being moved outwardly after the syringe is used. As is apparent from the description, the device disclosed by this patent is complex and would be difficult to assemble. No successful commercial product has resulted from the disclosure in this patent.

U.S. Pat. No. 5,385,551 discloses a non-reusable medical device that has a needle which is retractable by depression a plunger slidably mounted in the device. The disclosed device includes a front-mounted retraction mechanism that has a needle holder connected to the needle. The needle holder is supported along the axis of the device by a frictionally engaged retainer ring member coupled to the needle holder along an axially aligned sliding interface. The needle holder and retainer are positioned in the front portion of a hollow body. The front of a movable member or plunger presses against the retainer member passing around the needle holder which cannot move forward, thereby separating the retainer from the needle holder. The separation occurs by gradually reducing the extent of the sliding interface area until the retainer member pops loose from the needle holder whereupon the needle holder and needle are retracted into a cavity in the plunger in response to a retraction force applied to the needle holder by a previously compressed spring. Again, the device disclosed in this patent is complex, difficult to manufacture and appears to have significant undeliverable dead volume. Attempts have been made to commercialize products from this disclosure with only limited success.

U.S. Pat. No. 5,407,436 discloses a hypodermic syringe that has a hollow needle that is automatically retractable after use. The disclosed syringe includes a one-piece body molding, has a main chamber for a plunger, sample container or drug cartridge, a forward chamber to house a spring to bias a needle holder, and internal latching formations to retain the needle holder with the spring compressed in the forward chamber until automatic retraction when the latching formations are released by end of plunger movement. The patent discloses that the sealing between the plunger and the body is accomplished by an over-sized plunger head that forces head and wall deformation. The disclosed spring has seals at both ends for the forward chamber. The patent teaches that the needle, its holder, spring and seals can be installed using a sliding guide. In using a syringe produced using this disclosure, the practitioner would need to exercise care when drawing and expelling a fluid during filling, because the retraction of the needle is activated by depressing the plunger sufficiently to engage cooperating latches. The engagement occurs at the bottom of the stroke to expel fluid from the syringe.

U.S. Pat. No. 5,769,822 discloses a non-reusable syringe with a hollow plunger that has a seal member thereon. The position of the plunger and the seal relative to the barrel permits the plunger, with sufficient strength, to carry applied pressure through the device during injection of a fluid and yet permit the seal disposed at one end of the plunger to have maximum sealing integrity between the plunger and a cylindrical barrel disposed around the exterior of the plunger to abate leakage of the liquid in a chamber within the barrel, as the plunger is manipulated from an expanded position to and expended position and thereafter to a third or collapsed position.

U.S. Pat. No. 6,010,486 discloses a retracting needle syringe that substantially prevents reuse of the syringe by destroying the plunger rod and the needle hub and additionally, retracts the needle into the plunger rod. The disclosed syringe includes provisions that upon fully depressing the plunger rod and applying distally directed axial force, a frangible portion of the inner hub is broken and the plunger tip dislodges to allow a spring to urge a cutter to open the chamber inside the plunger.

Most of the devices discussed in the above referenced disclosures are somewhat complex, and many require manufacture and assembly of parts with potentially difficult assembly or tight tolerance requirements. Many of the designs depend upon a careful application of forces by the practitioner to draw and expel fluids from the syringe. Also, if the tolerances between the multiple components of the device are not carefully adhered to during manufacture and assembly, normal usage may result in premature activation of the retraction function of the syringe. Current conventional syringes are considered by users to be virtually fault-free and reliable. They are used for a variety of different procedures involving both "one-shot" fill and inject procedures, as well as more complex mixing, measuring and delivery functions. In order for a retractable syringe to displace these functional, utilitarian and reliable conventional syringes, the retractable syringe should not significantly interfere with the users current practices, it needs to be substantially reliable and its cost should not be prohibitive. Current conventional syringes are often manufactured at rates of several hundred per minute and their cost is generally not a significant factor in their usage. Additionally every year, hundreds of millions of small capacity (one milliliter) syringes are used outside of the normal controlled health care environment by diabetics and other self-injectors who must daily accurately inject small amounts, often only a few tenths of a milliliter. These small capacity syringes are physically quite small, with an overall length of less than five inches and an inside bore diameter of less than one-quarter inch. Reviewing the disclosures above, one skilled in the art of high volume manufacturing recognizes that assembling hundreds of millions of most of these relatively complex devices with their retraction elements contained in such a small space as a one-quarter inch diameter bore is a daunting task. Additionally, many of the disclosed devices have substantial undeliverable "dead volumes" that substantially confound many diabetics' need for accurate measuring, mixing of more than one type of insulin in the syringe and delivering small doses of insulin. The need thus exists for a selectively retractable syringe that is compatible with a small capacity syringe, that is capable of being manufactured at high volumes and is sufficiently non-complex to be reliable in use when produced at volumes of hundreds of millions per year. Such a device is disclosed herein below.

SUMMARY

A hypodermic syringe with a selectively retractable needle of the present invention includes an elongate barrel having an open proximal end and a distal end that defines a receiver with an inwardly projecting shoulder. The barrel has a hollow bore therethrough and the receiver further includes a plurality of inwardly projecting cams disposed distally to the shoulder. The syringe has an elongate plunger with a proximal end and a distal end. The plunger is sized to fit slidably within the hollow bore of the barrel to define a chamber for drawing and expelling fluid. There is a hub with a flange and a stem that has a passageway therethrough. The flange is sized to fit slidably through the open proximal end of the barrel with the stem extending distally into the receiver. The stem has distal recesses sized and disposed to engage the projecting cams in a cam-follower relationship between a first position, wherein the hub is retained so that the distal end of the stem is in the receiver with the flange defining a distal end of the chamber, and a second position. The syringe includes an elongate needle having a sharpened distal point, a proximal end and a fluid path therethrough. The proximal end of the needle is mounted in the passageway in the hub so that the distal point projects distally outwardly and the fluid path is in communication with the chamber. There is a clip disposed about the elongate plunger. The clip is initially disposed to allow proximal and distal movement of the plunger for drawing and expelling fluid from the chamber. When a distal force, greater than the force necessary to expel fluid from the chamber, is applied to the plunger thereby moving the hub distally beyond the first position so that the hub is rotated to the second position by the cam/cam-follower interaction of the projecting cams and recesses, the clip is disposed then to engage substantially irreversibly the proximal end of the barrel in a one-way relationship thereby further permitting only proximal movement of the plunger. The syringe of the invention further includes an elongate spring disposed about the stem and compressed between the flange and the inward shoulder to provide a bias between the shoulder and the flange. When a distal force, greater than the force required to expel fluid from the chamber, is applied to the flange by the plunger, the recesses in the stem by following the projecting cams in the cam/cam-follower relationship cause the rotation of the hub from the first position to the second position wherein the hub is no longer retained. Since the hub is no longer retained in the receiver, the bias of the spring urges a sufficient proximal movement of the hub, having the elongate needle mounted therein, into the hollow bore of the barrel as the plunger is moved proximally in the barrel thus withdrawing the sharpened distal point of the needle into the barrel. By withdrawing the needle into the barrel, inadvertent exposure of the sharpened distal point is substantially prevented. Additionally, since the engagement of the clip with the proximal end of the barrel substantially prevents distal movement of the plunger, it cannot be moved distally, rendering the syringe substantially non-functional.

The syringe of the invention has an undeliverable "dead-space" volume substantially similar to conventional syringes, i.e., substantially no undeliverable volume. The syringe of the invention is as suitable for use in drawing, measuring, mixing and delivering small volumes of medicaments as conventional syringes. Unlike many of the devices disclosed above, the syringe of the invention is substantially unlikely to be inadvertently retracted by a user following currently used practices and procedures. The syringe of the invention does not depend on a user having to exercise substantially more care than with a conventional syringe when drawing and mixing fluids in the syringe to avoid inadvertent activation, and importantly, the syringe of the invention is compatible with the efficiency of high volume automated manufacture that utilizes much existing manufacturing equipment. Once needle is retracted in the syringe of the invention, the syringe cannot be restored to functionality, as the hub flange is withdrawn into the syringe barrel and the plunger is substantially prevented from being moved distally back into the barrel, thus rendering syringe substantially unusable and protecting the needle point from inadvertent contact.

BRIEF DESCRIPTION OF THE DRAWINGS

FIG. 3 is a perspective view of the syringe of FIG. 1 illustrating the syringe in normal use;

FIG. 3a is an enlarged perspective view of a distal portion of the syringe of FIG. 3;

FIG. 4 is a perspective view of the syringe of FIG. 3 illustrating the beginning of the needle retraction;

FIG. 7 is a cross sectional view, taken from FIG. 4 along the line 7—7, illustrating the beginning of needle retraction;

FIG. 7a is an enlarged cross-sectional view of a proximal portion of the syringe of FIG. 7 with the clip fully engaging the proximal end of the barrel;

FIG. 8 is a cross-sectional view, analogous to FIG. 7, of the syringe of the invention illustrating the plunger withdrawn proximally and the needle withdrawn into the barrel;

FIG. 8a, is an enlarged cross-sectional view, taken from FIG. 8, of the distal portion of the syringe of FIG. 8;

DETAILED DESCRIPTION

Figure 1:
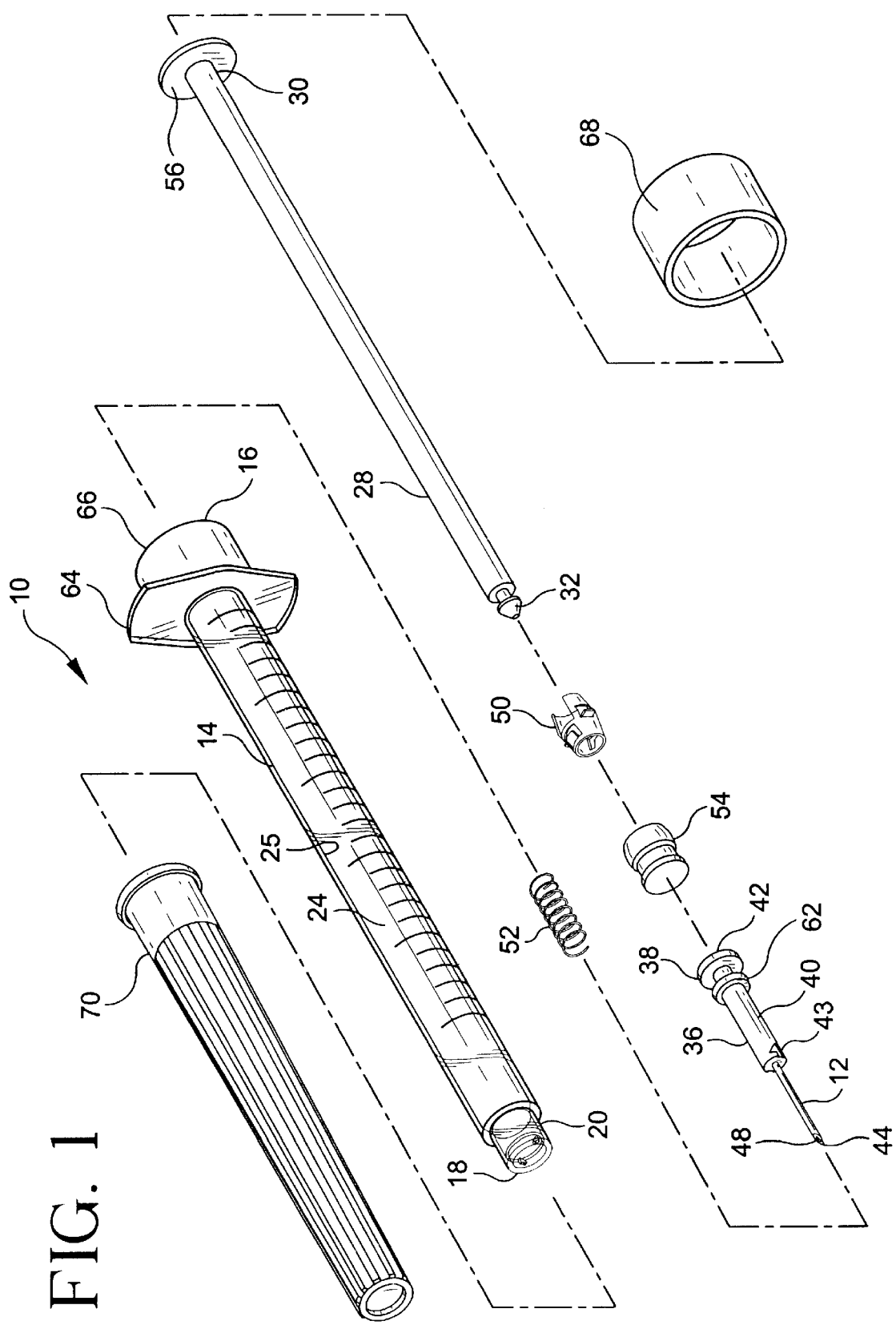
FIG. 1 is an exploded perspective view of the syringe of the invention.

While this invention is satisfied by embodiments in many different forms, there are shown in the drawings and herein described in detail, embodiments of the invention with the understanding that the present disclosure to be considered as exemplary of the principles of the present invention and is not intended to limit the scope of the invention to the embodiments illustrated. The scope of the invention is measured by the appended claims and the equivalents. In this disclosure, a convention is followed wherein the distal end of the device is the end closest to a patient and the proximal end of the device is the end away from the patient and closest to a practitioner.

Referring to the FIGS. 1–11, a hypodermic syringe 10 of the present invention with a selectively retractable needle 12 includes an elongate barrel 14 having an open proximal end 16 and a distal end 18 that defines a receiver 20 with an inwardly projecting shoulder 22. Barrel 14 has a hollow bore 24 therethrough and receiver 20 further includes at least one and, preferably, a plurality of inwardly projecting cams 26 disposed distally to shoulder 22. In a most preferred embodiment, there are two inwardly projecting cams 26. Syringe 10 has an elongate plunger 28 with a proximal end 30 and a distal end 32. Plunger 28 is sized to fit slidably within hollow bore 24 of the barrel to define a chamber 34 for drawing and expelling fluid. There is a hub 36 with a flange 38 and a stem 40 that has a passageway 42 therethrough. Flange 38 is sized to fit slidably through open proximal end 16 of the barrel with stem 40 extending distally into receiver 20. Stem 40 has distal recesses 43 sized and disposed to engage projecting cams 26 in a cam-follower relationship between a first position, best seen in FIGS. 3 and 3a, wherein hub 36 is retained so that the distal end of stem 40 is in receiver 20 with the flange 38 defining a distal end of chamber 34, and a second position best seen in FIGS. 4 and 4a. Elongate needle 12 has a sharpened distal point 44, a proximal end 46, shown in phantom in FIG. 4a, and a fluid path 48 therethrough. Proximal end 46 of the needle is mounted in passageway 42 in the hub so that distal point 44 projects distally outwardly and fluid path 48 is in communication with chamber 34. There is a clip 50 disposed about elongate plunger 28. Clip 50 is initially disposed to allow proximal and distal movement of plunger 28 for drawing and expelling fluid from chamber 34. When a distal force, greater than the force necessary to expel fluid from chamber 34, is applied to plunger 28 thereby moving hub 36 distally beyond the first position so that hub 36 is rotated to the second position by the cam/cam-follower interaction of the projecting cams and recesses, clip 50 is disposed then to engage, substantially irreversibly, proximal end 16 of the barrel in a one-way relationship thereby further permitting only proximal movement of plunger 28. Syringe 10 further includes an elongate spring 52 disposed about stem 40 and compressed between flange 38, preferably between a stem stop 62 located distally to flange 38, and inward shoulder 22 to provide a bias between shoulder 22 and flange 38. When a distal force, greater than the force required to expel fluid from chamber 34, is applied to flange 38 by plunger 28, recesses 43 in the stem by following projecting cams 26 in the cam/cam-follower relationship cause the rotation of hub 36 from the first position to the second position where hub 36 is no longer retained in receiver 20. Since hub 36 is no longer retained in receiver 20, the bias of spring 52 urges a sufficient proximal movement of hub 36, having elongate needle 12 mounted therein, into hollow bore 24 of the barrel as plunger 28 is moved proximally in the barrel thus withdrawing sharpened distal point 44 of the needle into barrel 14. By withdrawing needle 12 into barrel 14, inadvertent exposure of sharpened distal point 44 is substantially prevented. Additionally, since the engagement of clip 50 with proximal end 16 of the barrel substantially prevents distal movement of plunger 28, it cannot be moved distally, rendering syringe 10 substantially non-functional.

Preferably, distal end 32 of plunger 28 a stopper 54 formed from a resilient material that is sized and shaped to form a substantially fluid tight seal with an inside surface 25 of hollow bore 24 of the barrel, thereby facilitating drawing and expelling fluid from chamber 34. Suitable materials for forming stopper 54 include, but are not limited to, natural rubber, synthetic rubber, thermoplastic elastomers and combinations of these materials.

Figure 5:
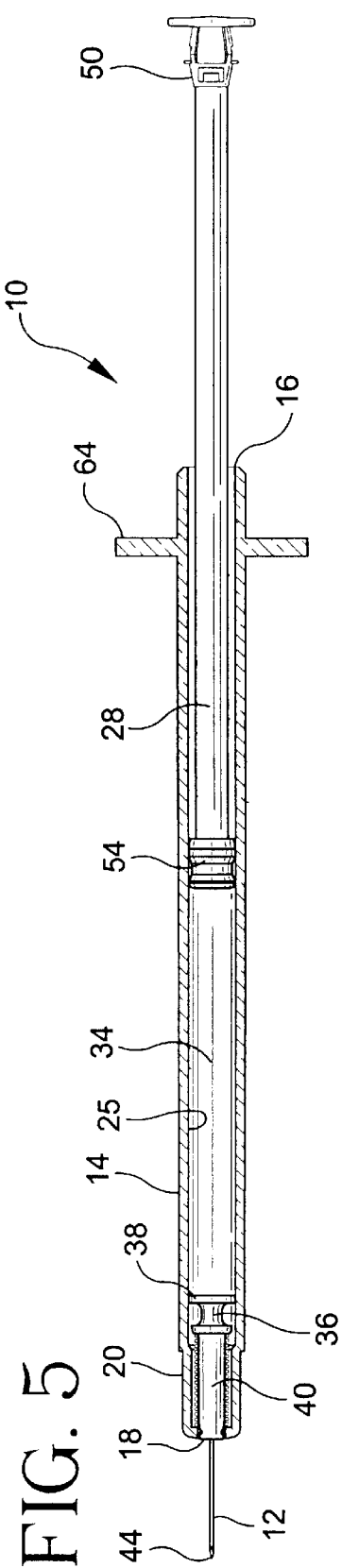
FIG. 5 is a cross-sectional view of the syringe of FIG. 3, taken along the line 5—5.
Figure 5A:
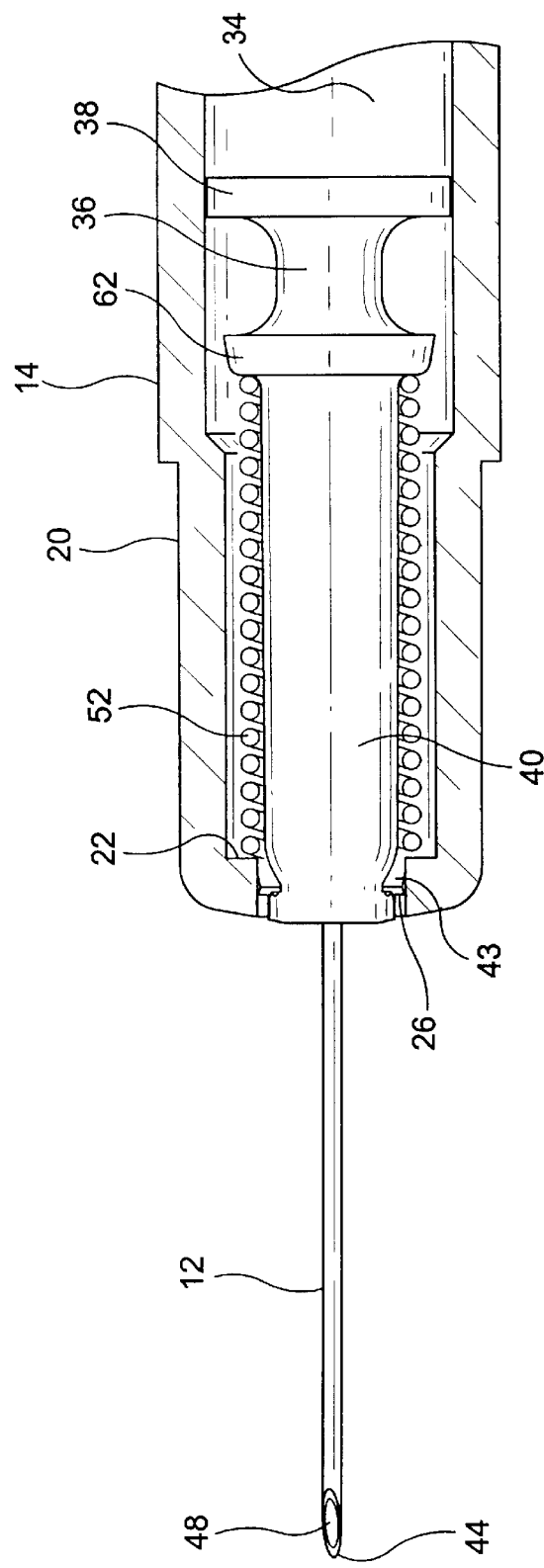
FIG. 5a is an enlarged cross-sectional view of a distal portion of the syringe of FIG. 5.
Figure 6:
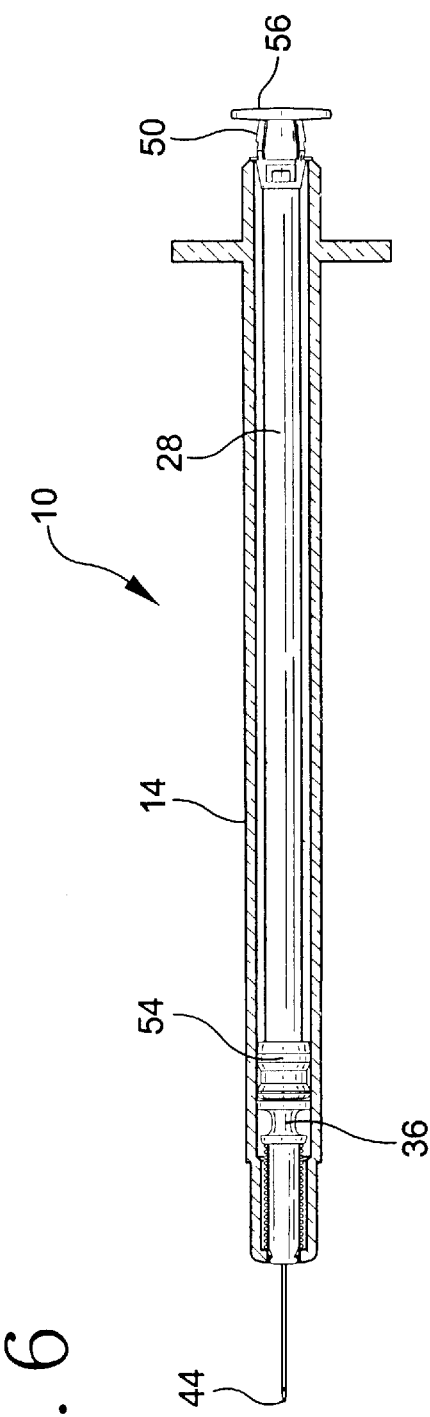
FIG. 6 is a cross-sectional view, analogous to FIG. 5, of the syringe of FIG. 1 with the clip prior to engaging the proximal end of the barrel.
Figure 6A:
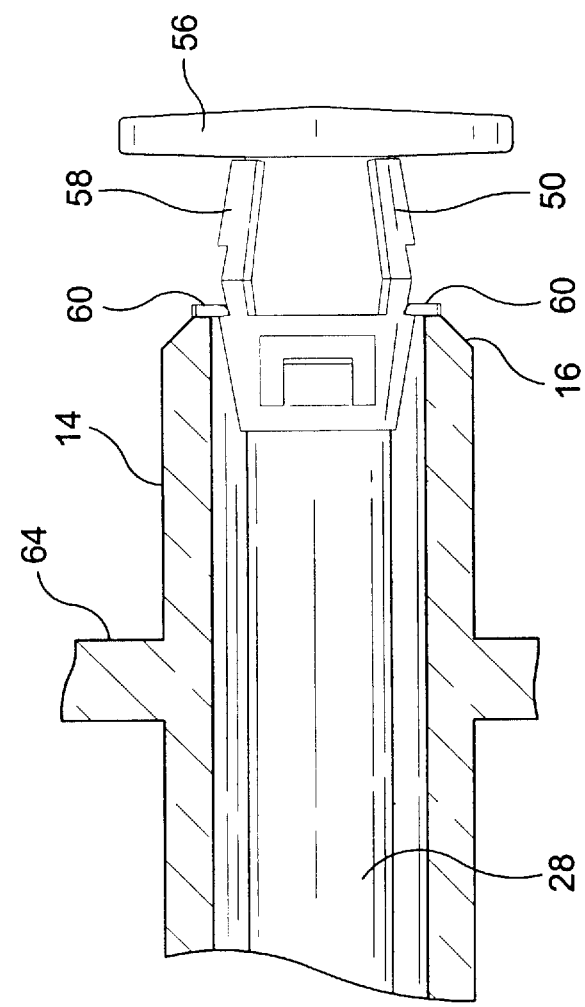
FIG. 6a is a cross-sectional view, analogous to FIG. 5a, of a proximal portion of the syringe of FIG. 6.
Figure 9:
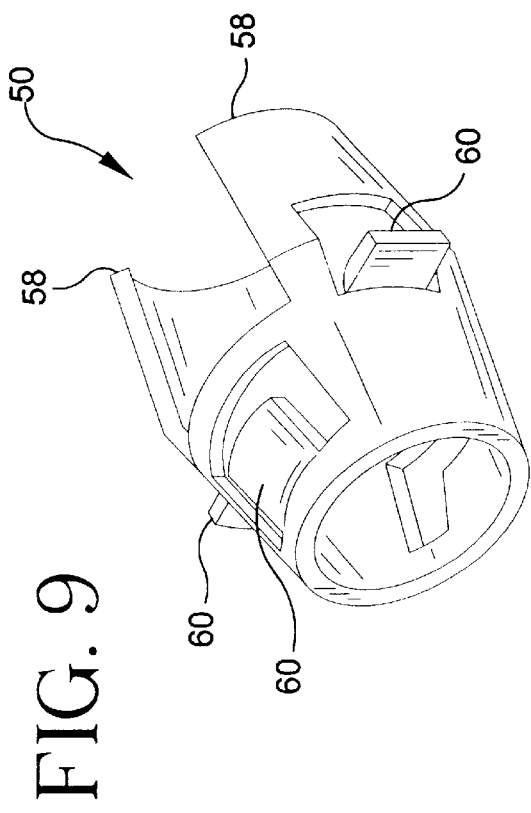
FIG. 9 is an enlarged perspective view of the clip portion of the syringe of FIG. 1.

Plunger 28 preferably includes a finger press portion 56 located at distal end 32. Referring now to FIGS. 3, 5 and 6, clip 50 is located proximally on plunger 28 so that the clip does not engage proximal end 16 of the barrel during normal proximal and distal movement of the plunger to draw and expel fluid from chamber 34. Clip 50 preferably includes at least two projections 58, best seen in FIG. 9, that are disposed to retain clip 50 on said plunger in the proximal position so that said clip does not engage barrel proximal end 16 during the normal proximal and distal movement of said plunger required to draw fluid into and expel fluid from chamber 34. Clip 50 also preferably includes at least two ears 60, again best seen in FIG. 9, that are disposed to engage proximal end 16 of the barrel substantially non-releasably, best seen in FIGS. 7 and 7a, when force, greater than the force required to expel fluid from chamber 34, is applied to plunger 28 thereby moving 34 hub to the second position and releasing said hub from receiver 20. Referring now to FIGS. 8 and 8a, as plunger 28 is moved distally, spring 52 urges hub 36 with needle 12 proximally into chamber 34 as plunger 28 is moved proximally in the barrel. Clip 50 is retained in proximal end 16 of the barrel by the action of ears 60, while projections 58 allow substantially only proximal movement of plunger 28 with respect to barrel 14. FIG. 8a illustrates receiver 20 with inwardly projecting cams 26 remaining after hub 36 is withdrawn.

Preferably, clip 50 is formed from a metallic material such as a stainless steel by a deep drawing process. Treatments of finished clip 50 by electrochemical polishing or other treatment to passivate, clean and sharpen the edges of the ears and projections may be preferred for particular applications.

Figure 10:
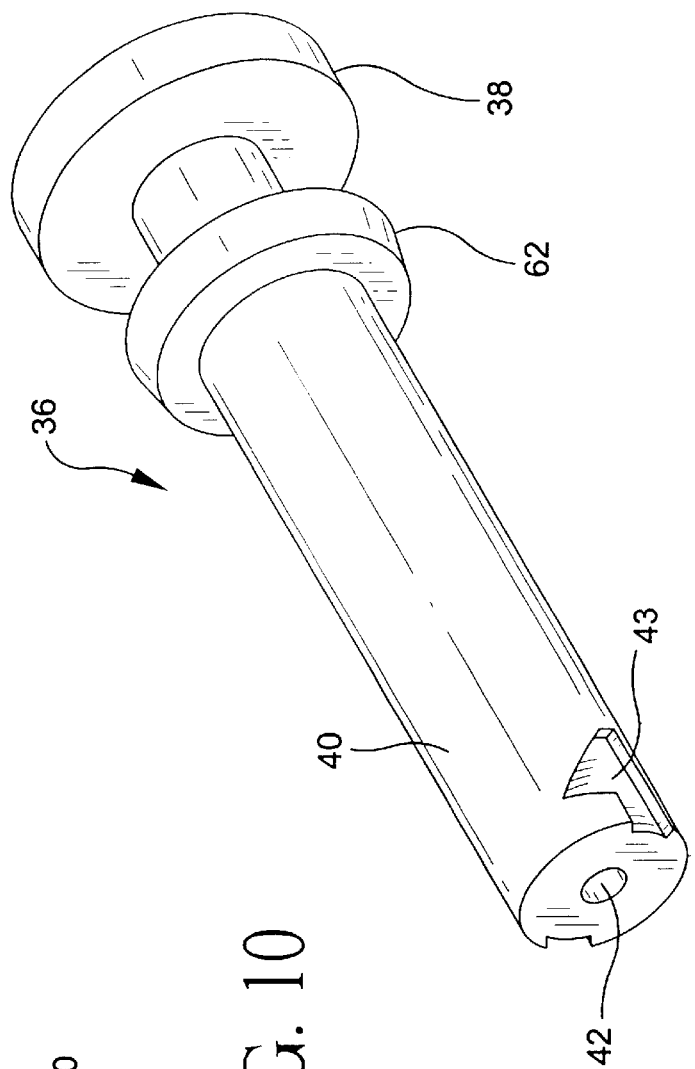
FIG. 10 is an enlarged perspective view of the hub portion of the syringe of FIG. 1.
Figure 11:
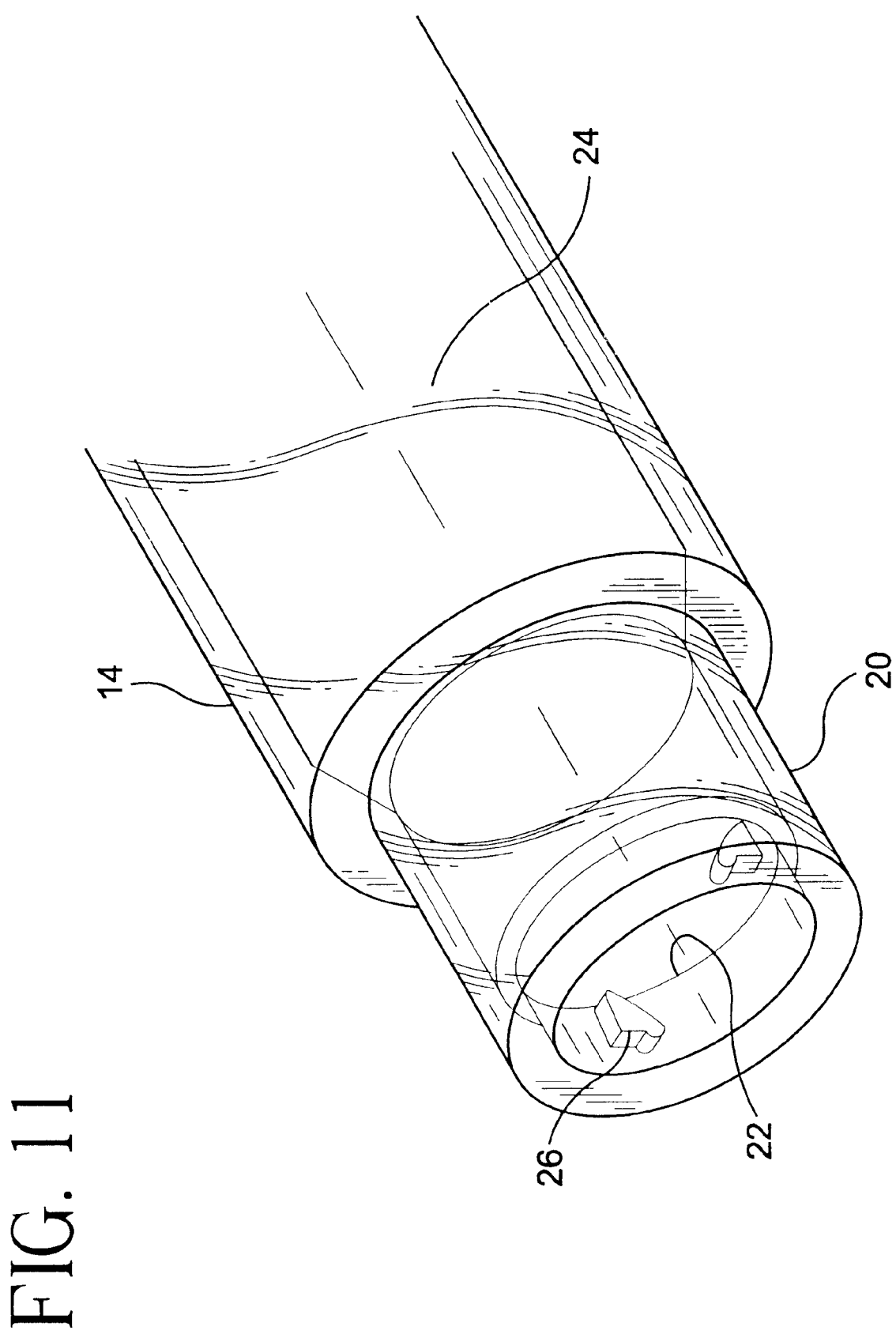
FIG. 11 is an enlarged perspective view of the distal portion of the barrel of the syringe of FIG. 1.

Referring now to FIG. 10, hub 36 with recesses 43 that are disposed to interact with inwardly projecting cams 26 is illustrated. Hub 36 preferably also includes stop 62 located stem 40 distally to flange 38 to engage spring 52 and to assist in keeping stem 40 substantially axially positioned in receiver 20 when force, greater than the force required to expel fluid from chamber 34, is applied to flange 38 to cause rotation of hub 34 from the first position, best seen in FIG. 3a, to the second position, best seen in FIG. 4. The interaction between cams 26 and recesses 43 when hub 36 is moved distally results in rotation of the hub with respect to barrel 14. This rotation of hub 36 then allows spring 52 to urge proximal movement of the hub with the needle mounted therein proximally into chamber 34 as plunger 28 is moved proximally.

A particular benefit of the design of hub 36 with stem 40 and spring 52 is seen during assembly of the several components into barrel 14. Preferably, an assembly pin is inserted into barrel 14 from distal end 18. Hub 36 is then acquired by an assembly mandrel and spring 52 is placed onto one of the assembly pin or stem 40. Stem 40 and the assembly pin are then brought into contact and moved distally into bore 24 of the barrel so that recesses 43 engage cams 26 to retain spring 52 and hub 36 in receiver 20. The assembly pin and the assembly mandrel are then withdrawn. At this point, from a manufacturing assembly perspective, barrel 14 is not substantially different than a conventional barrel. This allows continued assembly on machinery substantially similar to equipment used to print scale markings on the barrels and to mount needle 12 in passageway 42 in the hub.

Preferably, proximal end 16 of barrel 14 includes a finger grip 64 to assist a user in grasping syringe 10. Finger grip 64 preferably also includes a collar 66 around plunger 28 that is sized and shaped to allow a cap 68 to be fitted over plunger 28. Syringe 10 also preferably includes a needle shield 70 sized to fit over receiver 20 and protect needle 12 prior to use of the syringe. Preferably, cap 68 and shield 70 are frangibly attached to collar 66 and receiver 20 respectively so that a user can be substantially assured that cap 68 and shield 70 have not been removed prior to the intended use of the syringe.

Figure 2:
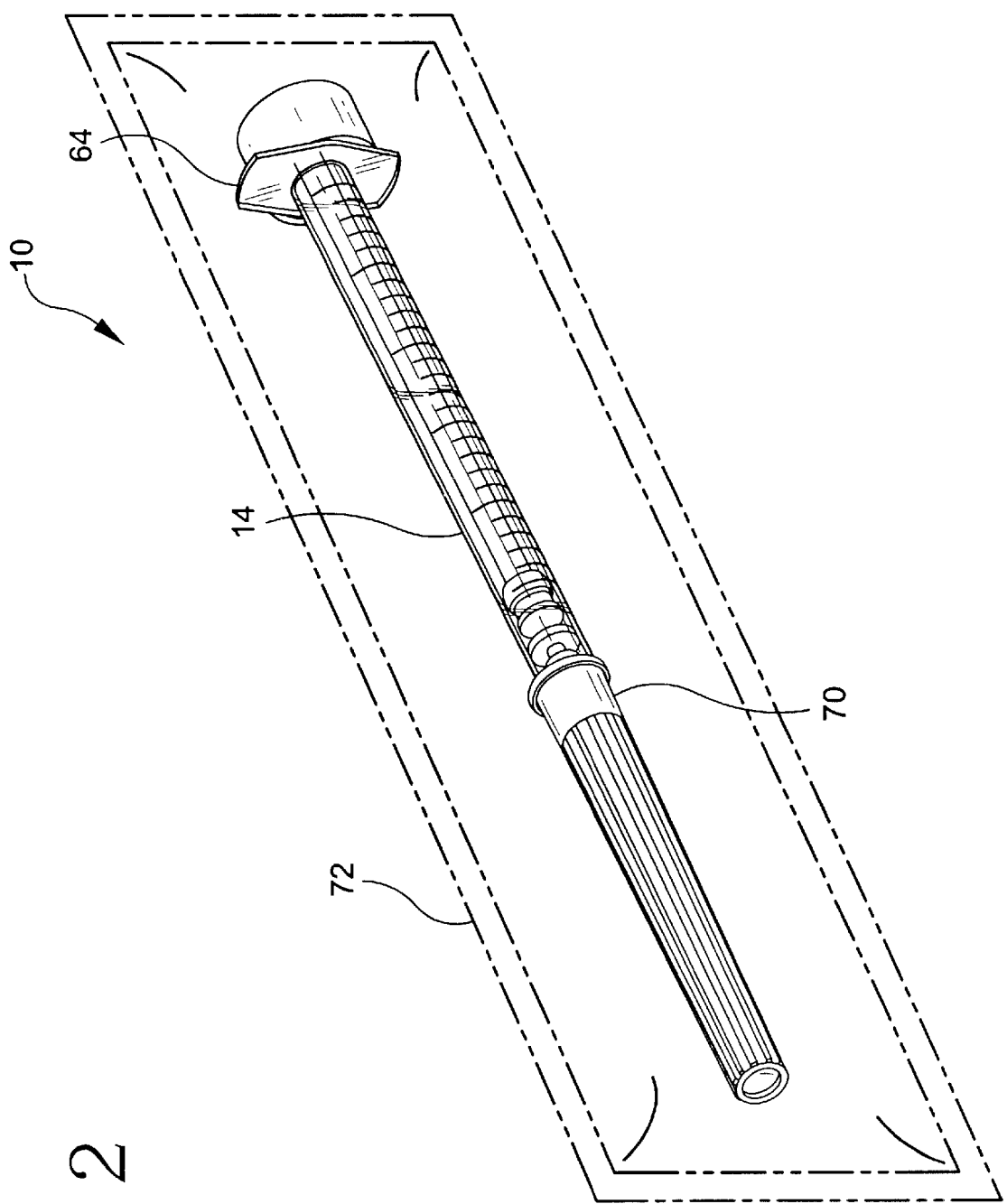
FIG. 2 is a perspective view of the syringe of FIG. 1 sealed in a package.
Figure 4A:
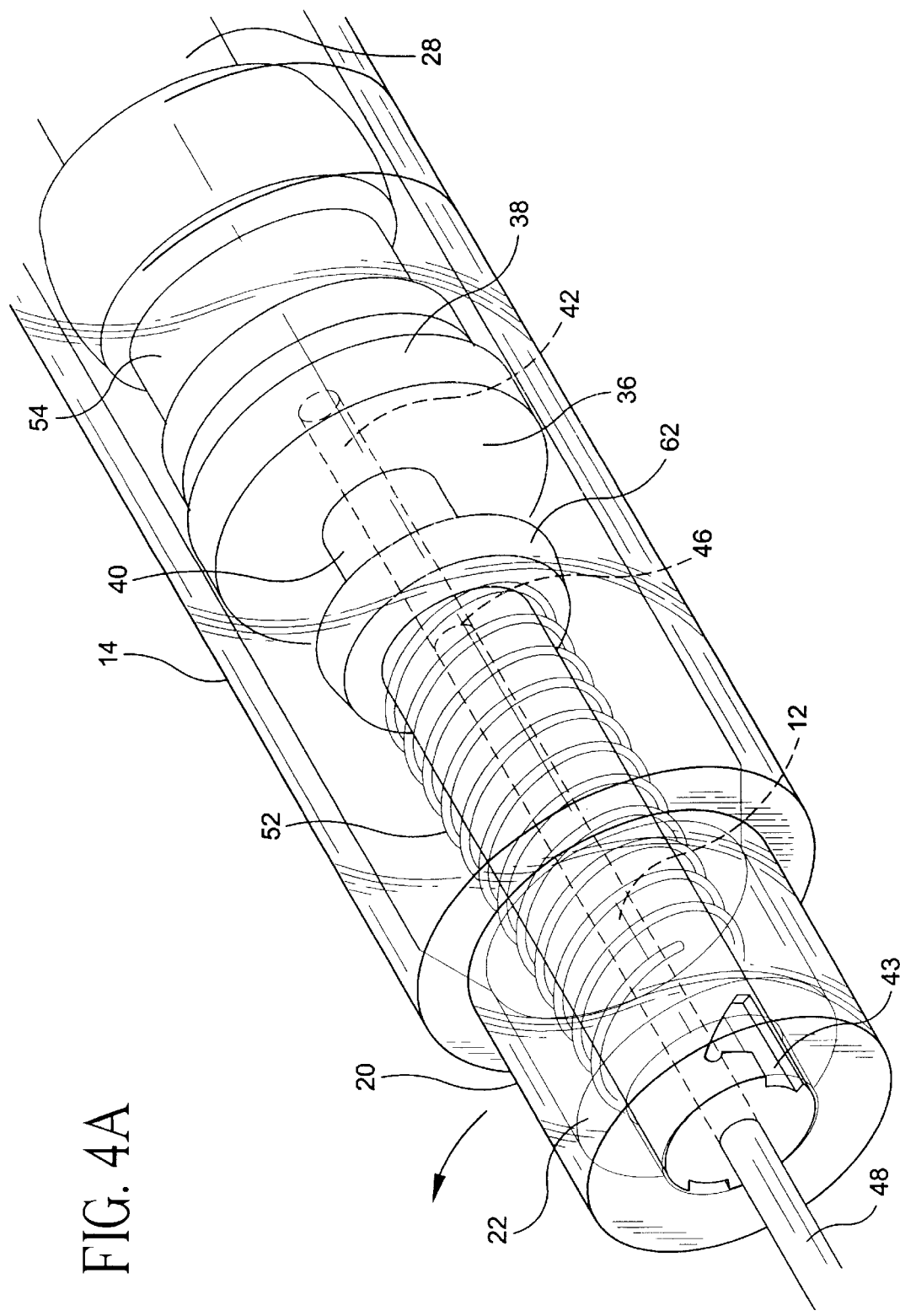
FIG. 4a is an enlarged perspective view of a distal portion of the syringe of FIG. 4.

Referring to FIG. 2, syringe 10 may be sealed in a package 72 formed from materials substantially resistant to the passage of microorganisms and exposed to conditions that render microorganisms substantially non-viable. Alternatively, when cap 68 and shield are in place, the fluid path of syringe 10 is substantially protected from microorganisms and syringe 10 may be exposed to conditions that render microorganisms substantially non-viable. Suitable conditions for rendering microorganisms substantially non-viable include, but are not limited to, exposure to ionizing radiation, chemical steriliants and the like. Suitable materials for forming package 72 include but are not limited to polymeric film, non-wovens, metallic foils, paper and combinations of these materials. Once placed in a package and exposed to these conditions, the product is labled sterile until the cap and shield are removed or the package is breached.

Suitable materials for forming barrel 14 include thermoplastic materials such as polypropylene, polyethylene, polycarbonate, polystyrene, copolymers and the like. Generally, a polypropylene material having radiation stabilizers is preferred. When materials are selected for forming syringe 10 and packaging 72, consideration should be given to the method to be used for sterilization to ensure compatibility of the materials with the sterilization method.

Many syringes are used in non-medical surroundings, these include insulin syringes, allergy syringes and syringes used in the administration of various hormones. Most of these usages require administration of small accurate doses. Syringes intended for these applications often have capacity of about one ml, have substantially no undeliverable volume and are less than about five inches long with a diameter of about one quarter inch. Many of the syringe designs disclosed in the background of the instant application are not compatible with such a physically small size and additionally have substantial undeliverable volume. Syringe 10 of the invention provides users of small capacity syringes with an easily manufactured design that is able to utilize similar assembly equipment to conventional syringes and additionally, adds the benefit that the use is substantially not different than conventional non-retractable syringes. Syringe 10 of the invention, once the use is completed, is selectively retractable by the user and is substantially non-reusable without physically destroying the clip retaining the plunger in the proximal position.

What is claimed is:

1. A hypodermic syringe with a selectively retractable needle comprising:

an elongate barrel having an open proximal end and a distal end defining a receiver with an inwardly projecting shoulder, said barrel having a hollow bore therethrough, said receiver further comprising at least one of inwardly projecting cam disposed distally to said shoulder;

an elongate plunger having a proximal end and a distal end, said plunger being sized to fit slidably within said hollow bore of said barrel to define a chamber for drawing and expelling fluid;

a hub comprising a flange and a stem, said hub having a passageway therethrough, said flange being sized to slidably fit through said open proximal end of said barrel with said stem extending distally into said receiver, said stem having distal recesses sized and disposed to engage said at least one projecting cam in a cam-follower relationship between a first position, wherein said hub is retained so that said distal end of said stem is retained in said receiver with said flange defining a distal end of said chamber, and a second position;

an elongate needle having a sharpened distal point, a proximal end and having a fluid path therethrough, said proximal end of said needle being mounted in said passageway in said hub so that said distal point projects outwardly and said fluid path is in communication with said chamber;

a clip disposed about said elongate plunger, said clip initially disposed to allow proximal and distal movement of said plunger for drawing and expelling fluid from said chamber, and wherein when a distal force, greater than the force necessary to expel fluid from said chamber, is applied to said plunger thereby moving said hub distally beyond said first position so that said hub is rotated to said second position by the cam/cam-follower interaction of said projecting cams and said recesses, said clip being disposed then to engage substantially irreversibly said proximal end of said barrel in a one-way relationship thereby further permitting only proximal movement of said plunger; and an elongate spring disposed about said stem and compressed between said flange and said inward shoulder to provide a bias between said shoulder and said flange so that when a distal force, greater than the force required to expel fluid from said chamber, is applied to said flange by said plunger, said recesses in said stem by following said projecting cams in said cam/cam-follower relationship cause the rotation of said hub from said first position to said second position wherein said hub is no longer retained and said bias of said spring urges a sufficient proximal movement of said hub having said elongate needle mounted therein into said hollow bore of said barrel as said plunger is moved proximally in said barrel to withdraw said sharpened distal point of said needle into said barrel thereby protecting said sharpened distal point from inadvertent exposure and, since said engagement of said clip with said proximal end of said barrel substantially prevents distal movement of said plunger, said plunger cannot be moved distally, rendering the syringe substantially non-functional.

2. The syringe of claim 1 wherein said distal end of said plunger further comprises a stopper sized and shaped to form a substantially fluid tight seal with an inside surface of said hollow bore of said barrel, thereby facilitating drawing and expelling fluid from said chamber.

3. The syringe of claim 2 wherein said stopper is formed from a resilient material selected from the group consisting of thermoplastic elastomer, natural rubber, synthetic rubber and combinations thereof.

4. The syringe of claim 1 wherein said proximal end of said elongate plunger further comprises a finger press to facilitate a user's movement of said plunger, said clip being initially positioned substantially adjacent said finger press so that until the force, greater than the force required to expel fluid from said chamber, is applied to said plunger, said clip does not engage said proximal end of said barrel.

5. The syringe of claim 1 wherein said proximal end of said barrel further comprises a finger grip and a collar.

6. The syringe of claim 5 further comprising a removable cap disposed on said collar and a removable shield disposed on said receiver.

7. The syringe of claim 6 further comprising said cap and said shield being frangibly attached to said collar and said receiver respectively, said syringe being exposed to conditions that substantially render any microorgasims therein non-viable, thereby providing a user a tamper-evidence indication that said syringe is substantially free from viable microorganisms as long as said cap and said shield have not been removed.

8. The syringe of claim 1 wherein said clip is formed from a metallic material comprising stainless steel.

9. The syringe of claim 8 wherein said clip is formed by a deep drawing process.

10. The syringe of claim 9 wherein said clip further comprises at least two projections that are disposed to retain said clip on said plunger in a proximal position so that said clip does not engage said barrel during proximal and distal movement of said plunger required to draw fluid into and expel fluid from said chamber, said clip further comprising at least two ears that are disposed to engage said proximal end of said barrel substantially non-releasably when force, greater than the force required to expel fluid from said chamber, is applied to said plunger thereby moving said hub to said second position and releasing said hub from said receiver so that as said plunger is moved proximally in said barrel, said spring urges said hub proximally into said bore of said barrel, said projections further being disposed to allow proximal movement of said plunger with respect to said engaged clip and substantially prevent distal movement of said plunger with respect to said engaged clip.

11. The syringe of claim 1 wherein said stem of said hub further comprises a stop disposed distally to said flange to engage said spring and to maintain said stem substantially axially in said receiver when said plunger engages said flange to cause said movement of said stem with respect to said receiver from said first position to said second position by said cam/cam-follower action of said recesses.

12. The syringe of claim 1 wherein said barrel is formed from a material selected from thermoplastics consisting of polypropylene, polyethylene, polycarbonate, polystyrene and copolymers thereof.

13. A hypodermic syringe with a selectively retractable needle comprising:

an elongate barrel having an open proximal end and a distal end defining a receiver with an inwardly projecting shoulder, said barrel having a hollow bore therethrough, said receiver further comprising a plurality of inwardly projecting cams disposed distally to said shoulder;

an elongate plunger having a proximal end and a distal end, said plunger being sized to fit slidably within said hollow bore of said barrel to define a chamber for drawing and expelling fluid;

a hub comprising a flange and a stem, said hub having a passageway therethrough, said flange being sized to slidably fit through said open proximal end of said barrel with said stem extending distally into said receiver, said stem having distal recesses sized and disposed to engage said projecting cams in a cam-follower relationship between a first position, wherein said hub is retained so that said distal end of said stem is retained in said receiver with said flange defining a distal end of said chamber, and a second position;

an elongate needle having a sharpened distal point, a proximal end and having a fluid path therethrough, said proximal end of said needle being mounted in said passageway in said hub so that said distal point projects outwardly and said fluid path is in communication with said chamber;

a clip disposed about said elongate plunger, said clip being retained in a proximal position by projections to allow proximal and distal movement of said plunger for drawing and expelling fluid from said chamber, and wherein when a distal force, greater than the force necessary to expel fluid from said chamber, is applied to said plunger thereby moving said hub distally beyond said first position so that said hub is rotated to said second position by the cam/cam-follower interaction of said projecting cams and said recesses, said clip being disposed then to engage substantially irreversibly said proximal end of said barrel in non-releasable relationship with two ears thereby further permitting only proximal movement of said plunger; and an elongate spring disposed about said stem and compressed between said flange and said inward shoulder to provide a bias between said shoulder and said flange so that when a distal force, greater than the force required to expel fluid from said chamber, is applied to said flange by said plunger, said recesses in said stem by following said projecting cams in said cam/cam-follower relationship cause the rotation of said hub from said first position to said second position wherein said hub is no longer retained and said bias of said spring urges a sufficient proximal movement of said hub having said elongate needle mounted therein into said hollow bore of said barrel as said plunger is moved proximally in said barrel to withdraw said sharpened distal point of said needle into said barrel thereby protecting said sharpened distal point from inadvertent exposure and, since said engagement of said clip with said proximal end of said barrel substantially prevents distal movement of said plunger, said plunger cannot be moved distally, rendering the syringe substantially non-functional.

\* \* \* \* \*